(12) United States Patent
Brandstrom

(10) Patent No.: US 7,804,295 B2  
(45) Date of Patent: Sep. 28, 2010

(54) APPARATUS AND METHOD FOR DETECTION OF DEFECTS USING FLUX LEAKAGE TECHNIQUES

(76) Inventor: Randel Brandstrom, 8713-53rd Avenue, Edmonton, Alberta (CA) T6E 5E9

(*) Notice: Subject to any disclaimer, the term of this patent is extended or adjusted under 35 U.S.C. 154(b) by 868 days.

(21) Appl. No.: 11/411,235

(22) Filed: Apr. 26, 2006

(65) Prior Publication Data

US 2006/0247868 A1 Nov. 2, 2006

Related U.S. Application Data

(60) Provisional application No. 60/675,480, filed on Apr. 28, 2005.

(51) Int. Cl. *G01N 27/82* (2006.01)
(52) U.S. Cl. .............. 324/228; 324/225; 324/238; 324/243
(58) Field of Classification Search ............ 324/228, 324/225, 238, 243
See application file for complete search history.

(56) References Cited

U.S. PATENT DOCUMENTS

| | | | |
|---|---|---|---|
| 4,789,827 A | 12/1988 | Bergander | |
| 5,030,911 A | 7/1991 | Lam | |
| 5,357,198 A | * 10/1994 | Ando et al. | ......... 324/242 |
| 5,614,825 A | 3/1997 | Maxfield et al. | |
| 5,619,136 A | 4/1997 | Drury | |

* cited by examiner

*Primary Examiner*—Reena Aurora  
(74) *Attorney, Agent, or Firm*—Adrian D. Battison; Ade & Company Inc.

(57) ABSTRACT

An apparatus for the detection of defects utilizing non-destructive flux leakage techniques in ferrous materials includes rare earth magnets which are supported at an angle in the order of 45 degrees with the surface of the test specimen to induce a magnetic field within the material. The angled arrangement draws the field into the specimen over a larger surface area, reducing reluctance and ensuring that the field does not shallow within the material. The device provides real-time, three dimensional, visual feedback to the user and includes built-in means for data storage and retrieval without the need for an external computer interface. A distance sensor is used to correct the signal from the sensor array for distance from the surface. A position analyzing device utilizes the magnetic field to determine the position of the apparatus along the surface of the test material, increasing the accuracy in position measurement during testing.

24 Claims, 3 Drawing Sheets

APPARATUS AND METHOD FOR DETECTION OF DEFECTS USING FLUX LEAKAGE TECHNIQUES

This application claims the benefit of priority under 35 U.S.C. 119 from Provisional Application 60/675,480 filed Apr. 28, 2005.

The present invention relates to an improved method and apparatus for the detection of defects utilizing non-destructive flux leakage techniques in ferrous materials.

BACKGROUND OF THE INVENTION

Flux leakage detection devices are used for detecting defects below the surface of objects made of ferromagnetic material, such as metal tubing or piping. Flat, curved or otherwise continuous ferrous bodies as well as continuous welds are also susceptible to inspection by this method. A magnetic field is induced in the body being inspected and an array of flux leakage sensors arranged in a predetermined geometry is used to detect changes in the magnetic field near the surface of the body. Discontinuities below the surface of a magnetized material are known to cause variations in the magnetic field above its surface and can therefore be detected by the sensor array. These devices are therefore passed over the surface area of the body being tested in order to locate defects therein. Prior art methods and devices for flux leakage detection have proven useful but leave much room for improvement in multiple areas.

U.S. Pat. No. 4,789,827 describes a magnetic flux leakage inspection unit for use on the inside of pipes and tubes. The device uses flux leakage coils to detect cracks and pits in the wall structure and a Hall Effect sensor to sense variation in wall thickness. Signals from the coils and sensor are fed through an external amplifier to a CRT, magnetic tape or strip chart recorder to generate usable output. The sensing device is limited by the types of objects it can be used to test, the type of data it can output and where it can be used due to the need for external equipment.

U.S. Pat. No. 5,030,911 describes a device for displaying defects in tubular members on a two-dimensional map. Longitudinal and circumferential position detectors are added to an existing inspection unit and the signals from the three devices are fed through an external computer programmed to process the signals and generate data including the longitudinal position, circumferential position, length, and angular orientation of the detected defects. The data can be displayed in both graph and table form using one or more display devices, including a CRT, chart recorder, plotter and/or printer. This testing method is limited by the types of objects it can test, the type of output it can provide and the sensing device's need for external equipment.

U.S. Pat. No. 5,614,825 describes a magnetic flux leakage inspection unit where the sensors are mounted in groups on blocks that are disposed to ride on the surface of the material under inspection. These blocks are mounted with a restricted degree of freedom for movement perpendicular to the test surface so that each individual block can independently respond to surface variations, reducing the degree of variation in the measured field caused by surface undulations and irregularities rather than internal defects. This arrangement is intended to improve accuracy in defect detection, but requires the regular replacement of sensor blocks due to wear caused by having them ride on the surface of the test specimen.

U.S. Pat. No. 5,619,136 describes a magnetic flux leakage inspection unit where a defect is detected when a differential output signal produced a coupled pair of sensors in the sensor array exceeds a threshold value. The device provides a warning signal to the user through LED lights connected to the sensors when a defect is detected, but does not provide for any other useful output data.

SUMMARY

According to a first aspect of the present invention there is provided an n apparatus for detecting discontinuities on or below a surface of a magnetizable material comprising:

a support arranged to be located adjacent the surface;

a drive arrangement for causing relative movement of the support along the surface;

a magnetizing device carried on the support for inducing a magnetic field in and above the material;

the magnetizing device including two opposing magnetic poles which are carried on the support so that axes of the poles are arranged so that the poles face the surface and the axes are directed generally toward the surface at spaced positions along the surface and are inclined inwardly toward each other so that the axis which is normal to its respective pole is not normal to the surface of the material;

an array or sensors carried on the support so as to be spaced from the surface where each sensor is arranged to detect magnetic flux leakage from the material and produce an output signal corresponding thereto;

and an analyzing device to detect the presence of discontinuities in the material based on the signals from the sensors and generate data on said discontinuities therefrom.

Preferably the magnetic poles are arranged such that the axis normal to its respective pole is incident with the surface of the material at an angle in the range of 45 degrees to less than 90 degrees.

Preferably the sensors are arranged in the array in rows.

Preferably there is provided a feedback device for each sensor in the array for buffering the signal from the respective sensor.

Preferably the array is located on the support so as to be presented to the surface between the poles.

Preferably the analyzing device comprises a calculating device for determining a first order spatial derivative of the signals from the sensors.

Preferably the analyzing device further comprises an examining device wherein the derivative is used to determine if the signals indicate discontinuities within the material.

Preferably there is provided a lift-off distance measuring device for continuously measuring the distance between the sensor array and the material surface and wherein the analyzing device is arranged to use the lift-off distance data to calibrate the signal from the sensors to the appropriate magnitude according to the lift-off distance.

Preferably the lift-off distance measuring device comprises:

a distance sensor installed on the sensor board and arranged to be perpendicular to the surface of the material;

a converter device for converting the analog signal from the distance sensor to a respective digital signal;

a communication device capable of carrying the digital distance signal from the converter device to the signal processing device.

Preferably the analyzing device includes a mechanical encoder device for tracking the position displacement as the apparatus travels along the surface of the material so that the relative position associated with a detected discontinuity can be added to the data on said discontinuity.

Preferably the mechanical encoder device comprises:

a rotating wheel device attached to the apparatus and adjusted to be constantly in contact with the surface of the material;

a converter device for converting the number of revolutions made by the rotating wheel as the apparatus proceeds onward into electrical signals;

a communication device capable of carrying the electrical signals from the converter device to the signal processing device.

Preferably the analyzing device includes a position analyzing device for determining a relative position of the apparatus along the surface of the material wherein the position information obtained by this position analyzing device is compared with the position information obtained by the mechanical encoder device for higher accuracy in position measurement.

Preferably the position analyzing device comprises a processing device for determining the relative position of the apparatus from calculating the position displacement of the recognized unique flux leakage features in the overlapping area of the sequential dataset detected by the sensor array.

Preferably there is provided a display device for displaying the data on each discontinuity as it is detected.

According to a second aspect of the invention there is provided an apparatus for detecting discontinuities on or below a surface of a magnetizable material comprising:

a support arranged to be located adjacent the surface;

a drive arrangement for causing relative movement of the support along the surface;

a magnetizing device carried on the support for inducing a magnetic field in and above the material;

an array or sensors carried on the support where each sensor is arranged to detect magnetic flux leakage from the material and produce an output signal corresponding thereto;

and an analyzing device to detect the presence of discontinuities in the material based on the signals from the sensors and generate data on said discontinuities therefrom;

and a lift-off distance measuring device for continuously measuring the distance between the sensor array and the material surface and wherein the analyzing device is arranged to use the lift-off distance data to calibrate the signal from the sensors to the appropriate magnitude according to the lift-off distance.

According to a third aspect of the invention there is provided an apparatus for detecting discontinuities on or below a surface of a magnetizable material comprising:

a support arranged to be located adjacent the surface;

a drive arrangement for causing relative movement of the support along the surface;

a magnetizing device carried on the support for inducing a magnetic field in and above the material;

an array or sensors carried on the support where each sensor is arranged to detect magnetic flux leakage from the material and produce an output signal corresponding thereto;

an analyzing device to detect the presence of discontinuities in the material based on the signals from the sensors and generate data on said discontinuities therefrom;

and a mechanical encoder device for tracking the position displacement as the apparatus travels along the surface of the material so that the relative position associated with a detected discontinuity can be added to the data on said discontinuity;

wherein the analyzing device includes a position analyzing device which utilizes the magnetic field to determine the position of the apparatus along the surface of the test material for determining a relative position of the apparatus along the surface of the material wherein the position information obtained by this position analyzing device is compared with the position information obtained by the mechanical encoder device for higher accuracy in position measurement The arrangement described hereinafter improves the quality of the flux leakage readings obtained by the sensors. The unique arrangement of positioning the magnetic poles at a predetermined angle with the test surface induces a high field density in the specimen with an ultra-low field in the region of the sensor array. This is due to the magnetic field encountering less reluctance when being drawn into the specimen over a greater surface area than in a typical flux leakage detector where the magnetic poles are normal to the surface.

The arrangement described hereinafter adds the capability of displaying real-time, three dimensional, visual feedback to the operator via a display monitor and storing and retrieving data without interfacing with external equipment.

In addition, the magnetic field used for detecting defects in the specimen is also used to track the position of the device via the position analyzing device. This position analyzing device serves as a complement to the mechanical position encoder for higher accuracy in position measurement.

DETAILED DESCRIPTION

Figure 1:
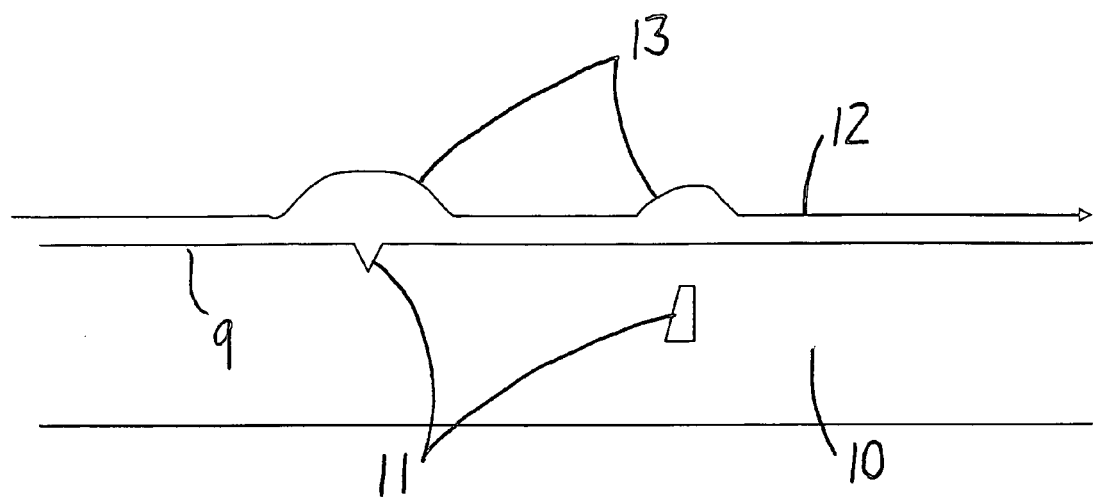
FIG. 1 is a prior art illustration of magnetic flux leakage caused by discontinuities within a test specimen.

The present invention is based on the concept that the magnetic field above the surface of a body of magnetizable material having a magnetic field induced therein will be of uniform flux except for where disturbed by the presence of discontinuities in the material, also known as flaws or defects. This concept is illustrated in FIG. 1 where the magnetizable test material 10 is shown with an upper surface 9. The magnetic flux above the surface 9, indicated by a line 12 remains uniform, as illustrated by the straight sections of the line, except at points where discontinuities are present at or beneath the surface 9 of the material 10. The disturbances 13 above the discontinuities 11 constitute leakage flux which can be detected using sensors disposed in proximity to the surface 9 of the material 10. A flux leakage detection device utilizes a magnetizing device for providing a magnetic field in the test material and an array of sensors for detecting leakage flux above the material's surface.

Figure 2:
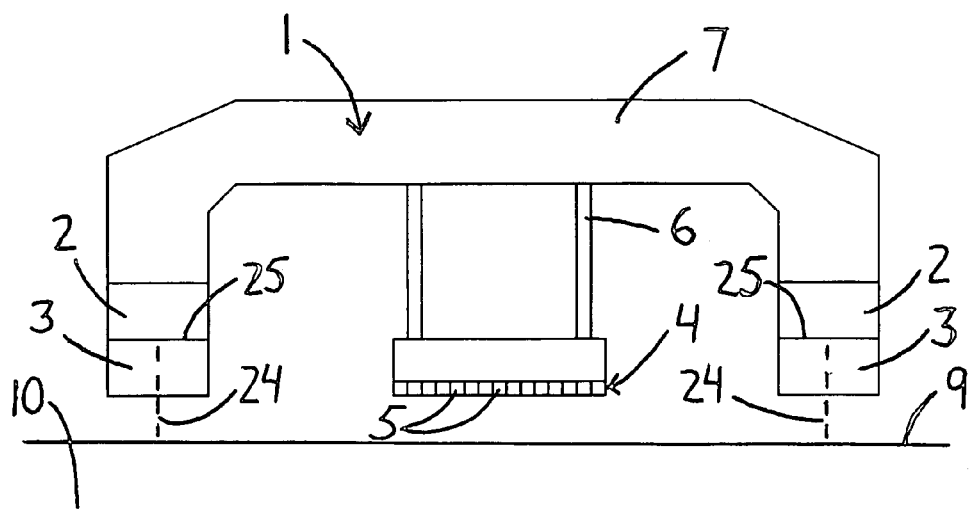
FIG. 2 is a side view of a typical prior art magnetizing device and sensor array used in prior art.

FIG. 2 illustrates a typical magnetizing device 1 for use in prior art flux leakage defect detection devices. Magnetic members 2 and respective pole pieces 3 for supplying the magnetic field in the test material 10 are supported on either end of a bridge member 7. An array 4 of sensors 5 is suspended between the pole pieces 3 by a mounting assembly 6 to detect flux leakage from the surface 9 of the test material 10. Note that each magnetic device 2 is arranged such that an imaginary axis 24 drawn normal to its lower surface 25 is normal to the upper surface 9 of the test material 10.

Figure 3:
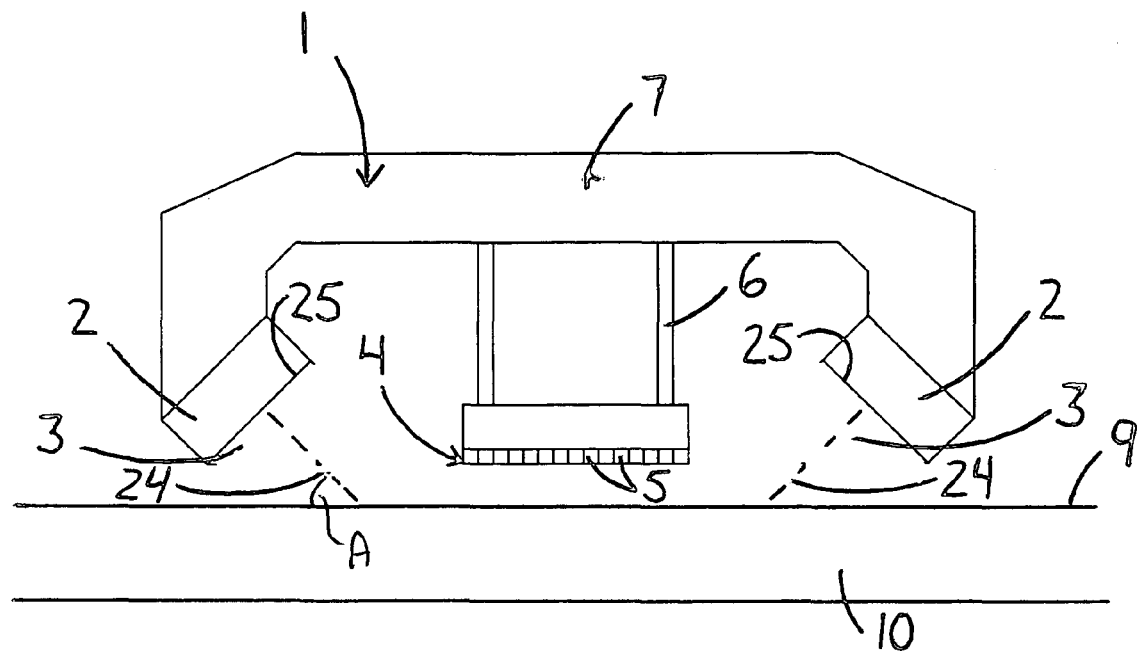
FIG. 3 is a side view of the magnetizing device, lift-off distance measuring device and sensor array of the present invention.
Figure 4:
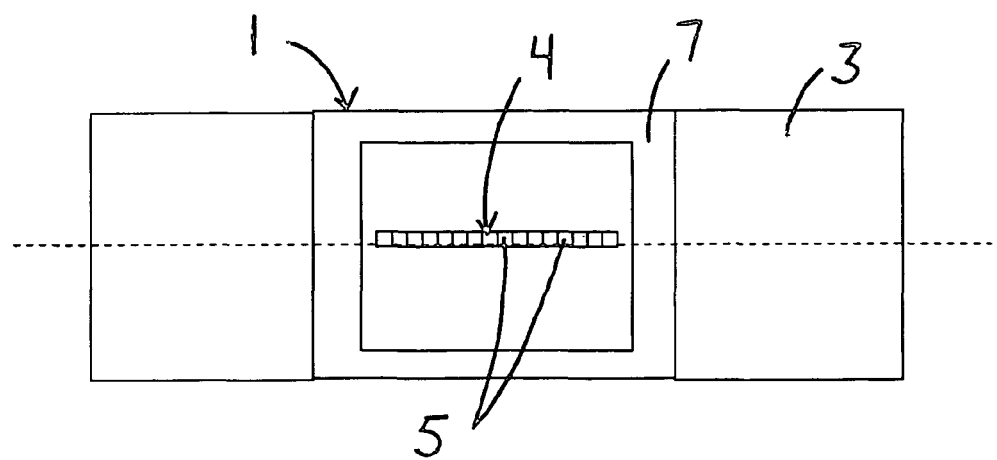
FIG. 4 is a bottom view of the magnetizing device, lift-off distance measuring device and sensor array of the present invention.

FIG. 3 illustrates the magnetizing device 1 of the present invention. The magnetic members 2 and respective pole pieces 3 are again supported on either end of the bridge member 7 so that the pole pieces form the ends of a horseshoe type magnet. They are oriented differently than in the prior art. The imaginary axis 24 drawn normal to the lower surface 25 of each pole piece is not normal to the test surface 9 of the test material 10. Instead, the axes 24 are inclined inwardly toward one another and downwardly to be incident on the surface 9 at an angle A which is less than 90 degrees and greater than 45 degrees with the preferred angle being preferably in the order of 45 degrees. This axis follows approximately the line of the magnetic field at the center of the magnet pole. Thus the lines of flux at the end surface 25 of the pole piece of the north and south poles of the magnet extend at right angles to the surface 25 and are incident on the surface 9 at the angle A.

This provides a greater surface area on the lower surface 25 of the pole pieces 3 which results in the magnetic field being drawn into the test specimen 10 over a larger area of its surface 9. This helps ensure that the field is drawn into the material 10 to a sufficient depth to provide adequate defect detection. As a result, the magnetic poles 3 can be positioned closer together than in prior art arrangements without having the field too shallow in the material 10.

The magnetizing device 1 and sensor array 4 are arranged to be movable over the surface 9 of the material 10 in order to be able to detect discontinuities over the entire surface area of the body of the test specimen.

A uniform magnetic flux is induced in the test specimen via the magnetizing device 1 such that the maximum amount of flux is induced in the interior of the target, while leaving a fairly low field in the external area above the surface 9 of the test specimen 10 when no defects are present. The magnetic members 2 are arranged such that their poles 3, and hence the magnetic field, meet the test specimen at the angle. This allows the field to draw into the specimen 10 at a lower reluctance since there is physically a larger surface area for the field to act over. Classic designs, where the poles meet the test specimen at 90 degrees, have the drawback that, if the poles are too close together, the field shallows in the test piece and creates an uneven flux distribution taking away the ability to see deep into the specimen. An added benefit of this design is that the inter-pole spacing, or the physical distance between the two poles 3 of the magnets 2, can be much smaller without having the field shallow. This is significant as it leads to a more compact design with very little compromise in uniformity of the test field.

The sensor array 4 is located on a mounting plate 6A carried on support arms 6B from the bridge member 7. The array resides at a fixed distance from the test target 10, between the poles of the magnets 2. The magnets 2 and the array 4 are aligned such that the magnetic field produced by the magnet is incident perpendicular to the active region of the sensors, thus capturing in the sensors the maximum amount of flux possible. Any magnetic perturbation caused by the presence of a defect or flaw 11, on or below the surface 9 of the test object 10, will cause a disturbance 13 in the magnetic field produced in the test object by the magnets 2.

The sensor array 4 comprises of a single or multiple rows of sensors 5 arranged in a geometric array residing on center between the two poles 3 of the magnets 2. Each sensor 5 is placed in the array 4 with predetermined optimal spacing between adjacent sensors. Each sensor 5 produces a signal corresponding to the amount of flux it detects.

The apparatus includes a lift-off distance measuring device 29 to continuously measure the varying lift-off distance between the sensor array 4 and the material surface 9. The varying lift-off distance affects the signal magnitude received by the sensor array. Without taking the varying lift-off distance into account, the change of the magnitude in the received signal can be misinterpreted as an indication of defect. By incorporating the lift-off distance data into the defect analysis process, the output data from the sensor array can be calibrated to the appropriate signal magnitude. Thus, the addition of the lift-off distance measuring device leads to higher accuracy in detecting detects.

Suitable devices for measuring the distance and providing an output signal proportional to the distance are well known and will be well apparent to a person skilled in the art. For example laser based measuring devices can be used and will provide a suitable output value.

Figure 5:
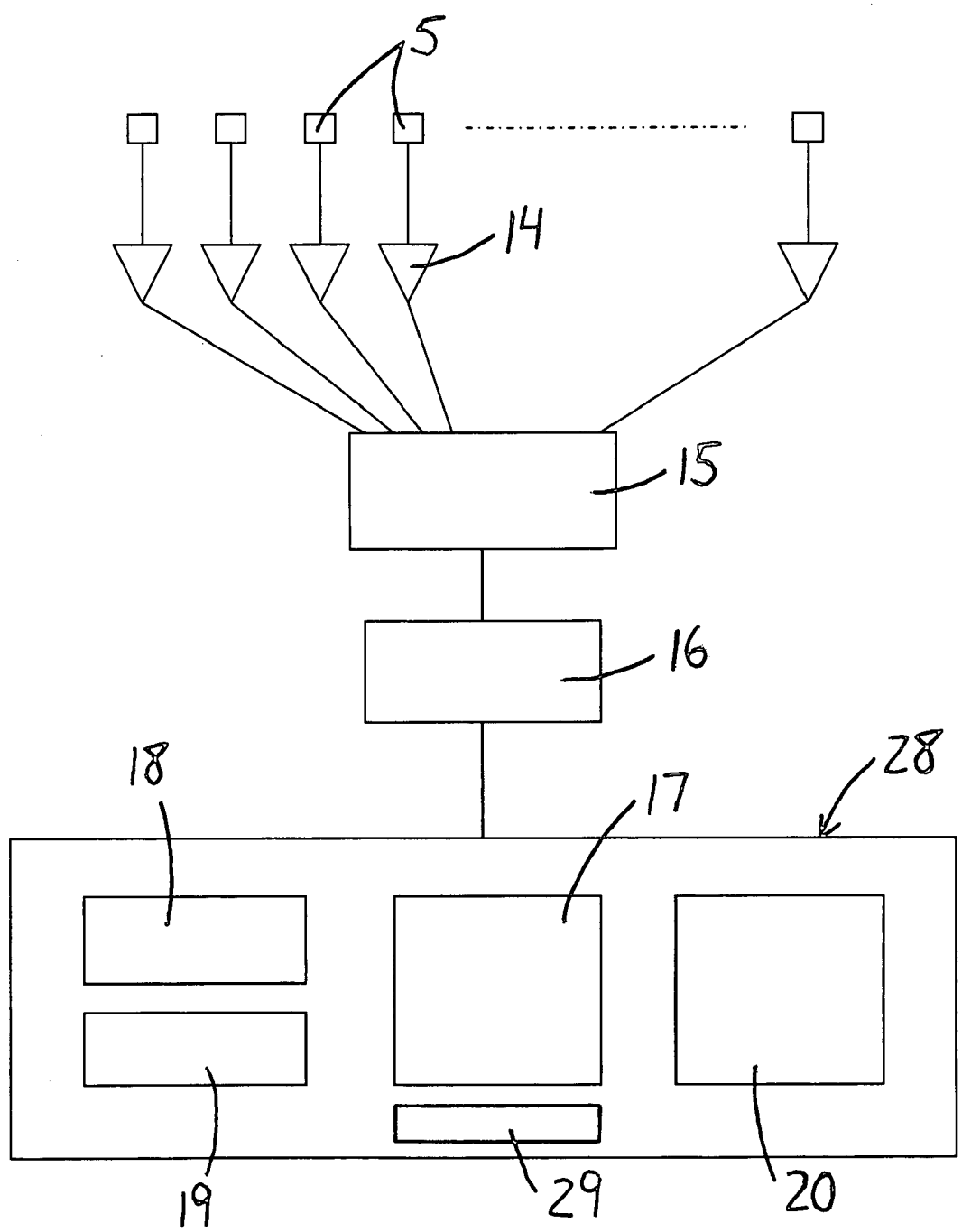
FIG. 5 is a diagram illustrating the connection of the devices involved in detecting defects in the test material and generating data thereon in the present invention.

As shown schematically in FIG. 5, the signal produced by each sensor 5 is individually buffered by a feedback circuit 14 and sent to an analog-to-digital converter 15. The converted signals from the sensors 5 are sent to a Field Programmable Gate Array (FPGA) 17 for further manipulation utilizing one of any digital communication gateways 16 (i.e. RS232, SPI, RS485, Ethernet, etc.). The FPGA 17 includes a microcomputer system 28 by which the data collected from the array 4 can be analyzed, stored, retrieved and displayed preferably without necessity for connection to outside data processors, although a connection may be available if data processing and/or data storage are required to be carried out externally.

The apparatus includes a mechanical encoder device 30 to track the position displacement as the apparatus travels along the surface of the specimen 10. This encoder device 30 is attached to the side of the magnetizing device 1. The encoder includes a rotating wheel 30A which is adjusted to be constantly in contact with the surface 9 and rotates as the apparatus moves onward. The encoder 30 includes a converter device of the encoder which converts the number of revolutions made by the rotating wheel into electrical signals. These signals are sent back to the signal processing device through a communication device. The obtained position displacement information is added to the data set and sent to the display device 19 and storage device 18.

The apparatus provides an additional means to track the position of the apparatus by utilizing the magnetic field. The position analyzing device utilizes the magnetic flux leakage recognition ability to monitor the position displacement of the flux leakage appearing in the received data set. To produce a data set suitable for the position analysis process, the sensor array 4 is placed above the specimen 10 and moves onward in an overlapping fashion. The FPGA 17 receives the signal data from the sensor array 4 and recognizes the unique leakage features in the overlapping area. By comparing the displacement of the recognized unique leakage features in the overlapping area in the next set of signal data detected by the sensor array, the FPGA 17 measures the position displacement of the apparatus. As the starting position of the device and the overlapping distance of the sensor array 4 are known to the FPGA 17, the detected defect positions can be accurately calculated and added to the data set and sent to the display device 19 and storage device 18.

The apparatus allows for fast data acquisition by utilizing a Field Programmable Gate Array (FPGA), which provides real-time, three-dimensional, visual feedback to the operator via a display monitor. The apparatus simplifies data interpretation by implementing automatic defect detection through advance algorithm design. The FPGA also allows for data storage and retrieval without the need for further computer interfaces.

Within the FPGA 17, data collected from the array is broken into predetermined chunk sizes and passed to a coded hardware device that has been pre-programmed to first filter the signal appropriately to minimize unwanted noise inevitably recorded along with the desired data and secondly calculate the first order spatial derivative along both the columns and rows of the array. The calculated derivative is then examined in software to determine if the minimum level of signal strength has been received that would indicate the presence of a defect within the data set. If a defect is indeed detected the device activates an alarm 29, which audibly and/or visually indicates that a defect has been discovered. All data, including the collected, analysed and raw data, is captured and stored on a non-volatile removable memory 18 for later archiving, retrieval and review. The raw data is also displayed on an appropriate display device 19 so that the operator can see, in real-time, what kind of data is being collected. This happens concurrently with the data analysis so that any detected flaws can be shown to the operator as they appear.

The device described above can satisfy a need for a magnetic flux leakage detection apparatus that can provide both a high degree of measurement accuracy without the added cost and downtime of replacing worn parts. In addition, the apparatus that can provide the user with detailed, easy to analyze output data without the need for external signal processing components.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. An apparatus for detecting discontinuities on or below a surface of a magnetizable material comprising:
   a support arranged to be located adjacent the surface;
   a drive arrangement for causing relative movement of the support along the surface;
   a magnetizing device carried on the support for inducing a magnetic field in and above the material;
   an array of sensors carried on the support where each sensor is arranged to detect magnetic flux leakage from the material and produce an output signal corresponding thereto;
   and an analyzing device to detect the presence of discontinuities in the material based on the signals from the sensors and generate data on said discontinuities therefrom;
   and a lift-off distance measuring device for continuously measuring a lift-off distance between the sensor array and the material surface so as to generate lift-off distance data and wherein the analyzing device is arranged to use the lift-off distance data to calibrate the signal from the sensors to the appropriate magnitude according to the lift-off distance.

2. The apparatus according to claim 1 wherein
   the magnetizing device includes two opposing magnetic poles which are carried on the support so that axes of the poles are arranged so that the poles face the surface and the axes are directed generally toward the surface at spaced positions along the surface and are inclined inwardly toward each other so that the axis which is normal to its respective pole is not normal to the surface of the material.

3. The apparatus according to claim 2 wherein the magnetic poles are arranged such that the axis normal to its respective pole is incident with the surface of the material at an angle in the order of 45 degrees.

4. The apparatus according to claim 2 wherein the sensors are arranged in the array in rows.

5. The apparatus according to claim 2 wherein the array is located on the support so as to be presented to the surface between the poles.

6. The apparatus according to claim 1 wherein there is provided a feedback device for each sensor in the array for buffering the signal from the respective sensor.

7. The apparatus according to claim 1 wherein the analyzing device comprises a calculating device for determining a first order spatial derivative of the signals from the sensors.

8. The apparatus according to claim 7 wherein the analyzing device further comprises an examining device wherein the derivative is used to determine if the signals indicate discontinuities within the material.

9. The apparatus according to claim 1 wherein the analyzing device includes a mechanical encoder device for tracking the position displacement as the apparatus travels along the surface of the material so that the relative position associated with a detected discontinuity can be added to the data on said discontinuity.

10. The apparatus according the claim 9 wherein the mechanical encoder device comprises:
    a rotating wheel device attached to the apparatus and adjusted to be constantly in contact with the surface of the material;
    a converter device for converting the number of revolutions made by the rotating wheel as the apparatus proceeds onward into electrical signals;
    a communication device capable of carrying the electrical signals from the converter device to the signal processing device.

11. The apparatus according to claim 1 wherein the analyzing device includes a position analyzing device for determining a relative position of the apparatus along the surface of the material wherein the position information obtained by this position analyzing device is compared with the position information obtained by the mechanical encoder device for higher accuracy in position measurement.

12. The apparatus according to claim 11 wherein the position analyzing device comprises a processing device for determining the relative position of the apparatus from calculating the position displacement of the recognized unique flux leakage features in the overlapping area of the sequential dataset detected by the sensor array.

13. The apparatus according to claim 1 wherein there is provided a display device for displaying the data on each discontinuity as it is detected.

14. The apparatus according the claim 1 wherein the lift-off distance measuring device comprises:
    a distance sensor installed on the sensor board and arranged to be perpendicular to the surface of the material;
    a converter device for converting the analog signal from the distance sensor to a respective digital signal;
    a communication device capable of carrying the digital distance signal from the converter device to the signal processing device.

15. An apparatus for detecting discontinuities on or below a surface of a magnetizable material comprising:
    a support arranged to be located adjacent the surface;
    a drive arrangement for causing relative movement of the support along the surface;
    a magnetizing device carried on the support for inducing a magnetic field in and above the material;

an array of sensors carried on the support where each sensor is arranged to detect magnetic flux leakage from the material and produce an output signal corresponding thereto;

an analyzing device to detect the presence of discontinuities in the material based on the signals from the sensors and generate data on said discontinuities therefrom;

and a mechanical encoder device for tracking the position displacement as the apparatus travels along the surface of the material so that the relative position associated with a detected discontinuity can be added to the data on said discontinuity;

wherein the analyzing device includes a position analyzing device which utilizes the magnetic field to determine the position of the apparatus along the surface of the test material for determining a relative position of the apparatus along the surface of the material wherein the position information obtained by this position analyzing device is compared with the position information obtained by the mechanical encoder device for higher accuracy in position measurement.

16. The apparatus according to claim 15 wherein the mechanical encoder device comprises:

a rotating wheel device attached to the apparatus and adjusted to be constantly in contact with the surface of the material;

a converter device for converting the number of revolutions made by the rotating wheel as the apparatus proceeds onward into electrical signals;

a communication device capable of carrying the electrical signals from the converter device to the signal processing device.

17. The apparatus according to claim 16 wherein the position analyzing device comprises a processing device for determining the relative position of the apparatus from calculating the position displacement of the recognized unique flux leakage features in the overlapping area of the sequential dataset detected by the sensor array.

18. The apparatus according to claim 15 wherein the magnetizing device includes two opposing magnetic poles which are carried on the support so that axes of the poles are arranged so that the poles face the surface and the axes are directed generally toward the surface at spaced positions along the surface and are inclined inwardly toward each other so that the axis which is normal to its respective pole is not normal to the surface of the material.

19. The apparatus according to claim 18 wherein the magnetic poles are arranged such that the axis normal to its respective pole is incident with the surface of the material at an angle in the order of 45 degrees.

20. The apparatus according to claim 18 wherein the array is located on the support so as to be presented to the surface between the poles.

21. The apparatus according to claim 15 wherein the sensors are arranged in the array in rows.

22. The apparatus according to claim 15 wherein there is provided a feedback device for each sensor in the array for buffering the signal from the respective sensor.

23. The apparatus according to claim 15 wherein the analyzing device comprises a calculating device for determining a first order spatial derivative of the signals from the sensors.

24. The apparatus according to claim 23 wherein the analyzing device further comprises an examining device wherein the derivative is used to determine if the signals indicate discontinuities within the material.

\* \* \* \* \*